United States Patent
Nalepa

(10) Patent No.: US 6,379,563 B1
(45) Date of Patent: Apr. 30, 2002

(54) ALKYLAMINES AS BIOFILM DEACTIVATION AGENTS

(75) Inventor: Christopher J. Nalepa, Baton Rouge, LA (US)

(73) Assignee: Albemarle Corporation, Richmond, VA (US)

( * ) Notice: Subject to any disclaimer, the term of this patent is extended or adjusted under 35 U.S.C. 154(b) by 0 days.

(21) Appl. No.: 09/487,743

(22) Filed: Jan. 19, 2000

(51) Int. Cl.[7] .................................................. C02F 1/50
(52) U.S. Cl. ........................ 210/764; 252/175; 422/28
(58) Field of Search ........................ 210/764; 252/175; 422/28

(56) References Cited

U.S. PATENT DOCUMENTS

| | | | |
|---|---|---|---|
| 3,719,763 A | 3/1973 | Cline et al. | 424/325 |
| 4,295,971 A | 10/1981 | Khalafalla et al. | 210/695 |
| 4,874,526 A | * 10/1989 | Grade et al. | |
| 5,411,666 A | 5/1995 | Hollis et al. | 210/632 |
| 5,817,888 A | 10/1998 | Elnagar et al. | 568/656 |
| 5,843,865 A | 12/1998 | Del Corral et al. | 504/160 |
| 5,902,820 A | 5/1999 | Jacquess et al. | 514/383 |
| 5,922,669 A | 7/1999 | Quebedeaux et al. | 510/421 |
| 5,935,518 A | * 8/1999 | Richard et al. | |
| 6,132,628 A | * 10/2000 | Barak | |

FOREIGN PATENT DOCUMENTS

| | | |
|---|---|---|
| WO | WO 99/13715 | 3/1999 |

OTHER PUBLICATIONS

Jon J. Kabara, et al., "Relationship of Chemical Structure and Antimicrobial Activity of Alkyl Amides and Amines"; Antimicrobial Agents and Chemotherapy, vol. 2, No. 6, Dec. 1972, pp. 492–498.

M.D. Culler, et al. "Mastitis: I. In Vitro Antimicrobial Activity of Alkyl Amines Against Mastitic Bacteria"; J Dairy Sci, 1979, 62: 584–595.

Victor D. Warner, et al., "Alkylamine Salts and Amides: In Vitro Inhibition of S mutans 6715"; J. Dent, Res., Dec. 1977, pp. 1599–1602.

D. Adams, et al., "The Use of Surfactants to Prevent Bacterial Adhesion ot Enamel"; Bacterial Adhesion and Preventative Dentistry, pp. 179–191.

Hendrick J. Hueck, et al., "Bacteriostatic, Fungistatic, and Algistatic Activity fo Fatty Nitrogen Compounds"; Applied Microbiology; American Society for Microbiology; May, 1966 vol. 14, No. 3 pp. 308–319.

Ferdinand Devinsky, et al., "Cut–off Effect in Antimicrobial Activity and in Membrane Perturbation Efficiency of the Homologous Series of N,N–Dimethylalkylamine Oxides"; J. Pharm, Pharmacol, Apr. 1990, 42: 790–794.

J.A. Findlay, et al.; "The Potential of Alkyl Amines as Antifouling Biocides I: Toxicity and Structure Activity Relationships"; Biofouling, 1996, vol. 9(4). pp 257–268.

A. Al–Hashem, et al.; "The Effects of Seasonal Changes on the Selection of Biocide Inhibitors for Arabian Gulf Seawater for Water Injection Purposes"; Corrosion 97, Paper No. 395.

\* cited by examiner

*Primary Examiner*—Betsey Morrison Hoey
(74) *Attorney, Agent, or Firm*—Philip M. Pippenger

(57) ABSTRACT

Aqueous industrial, recreational, and drilling systems comprising a biofilm deactivation agent consisting essentially of one or more alkylamines. The biofilm deactivation agent has a "minimum biofilm deactivation concentration" ("MBEC") of about 200 ppm or less. In a preferred embodiment, the biofilm deactivation agent consists essentially of primary alkylamines having from about 12 to about 14 carbon atoms, and a MBEC of about 50 ppm or less, most preferably about 30 ppm or less. A most preferred embodiment comprises a synergistic combination of specific quaternary ammonium salts with a primary alkylamine having from about 12 to about 14 carbon atoms. The invention also relates to the method of treating an aqueous system with these biofilm deactivation agents, either alone, or in the presence of an oxidizing agent for static control.

35 Claims, No Drawings

ALKYLAMINES AS BIOFILM DEACTIVATION AGENTS

FIELD OF THE INVENTION

The invention relates to agents for deactivating biofilms on surfaces in a variety of aqueous systems, including but not necessarily limited to recreational and industrial water systems, including drilling systems.

BACKGROUND OF THE INVENTION

Biological fouling is a serious economic problem in both industrial and recreational water systems. Biological fouling is the buildup of a "biofilm" on the surfaces that come into contact with the water in the system. A "biofilm" is the buildup of layers of microorganisms and/or extracellular substances and the dirt and/or debris that becomes trapped in that buildup. Bacteria, fungi, yeasts, diatoms and protozoa are only some of the organisms that cause the buildup of a biofilm.

In recreational waters, biofilms tend to be "slimey" to the touch, and can create a health hazard. In industrial waters, biofouling can interfere with industrial processes, lowering the efficiency of the process, wasting energy, and reducing product quality. In drilling systems, biofouling contributes to the corrosion of expensive drilling equipment.

Biofilm problems are encountered frequently in cooling water systems used in power- generating plants, refineries, chemical plants, and air conditioning systems. Cooling water systems commonly are contaminated with airborne organisms entrained by air/water contact in cooling towers as well as waterborne organisms from the system's makeup water supply. The water in such systems generally is an excellent growth medium for these organisms. If not controlled, the biofilm that results from such growth can plug towers, block pipelines, and coat heat transfer surfaces with layers of slime, thereby preventing proper operation and reducing the efficiency of the affected equipment.

Biofilms traditionally are controlled using oxidizing agents, which typically are based on chlorine or bromine. Oxidizing systems are effective to control biofilms, but such systems also can corrode valuable metal equipment and may irritate delicate and/or sensitive skin.

Non-oxidizing agents are available to control biofilms, and should avoid the foregoing problems; however, oxidizing biocides tend to be much more effective than non-oxidizing biocides at deactivating a biofilm. Biofilms also tend to require exposure to much higher doses of non-oxidizing agents for much longer periods of time than the dosage and time required to kill microorganisms in a suspension. As a result, non-oxidizing agents tend to be much more expensive to use as biofilm eradicating agents than oxidizing agents.

The current trend is towards using continuous levels of oxidizing biocides to maintain clean water system surfaces and to decrease the risk of contamination by *Legionella pneumophila*, the bacteria responsible for Legionnaire's disease. A continuous need exists for non-oxidizing biofilm agents for aqueous systems which are effective to deactivate biofilms at lower doses.

SUMMARY OF THE INVENTION

The invention provides an aqueous system comprising a biofilm deactivation agent consisting essentially of one or more alkylamines. In a preferred embodiment, the biofilm deactivation agent also comprises a synergistically effective combination of the alkylamine with specified monomeric quaternary ammonium salts. The biofilm deactivation agent has a "minimum biofilm deactivation concentration" of about 200 or less. The invention also relates to the method of treating an aqueous system with the biofilm deactivation agent.

DETAILED DESCRIPTION OF THE INVENTION

Very low concentrations of certain alkylamines completely deactivated biofilm bacteria during laboratory testing, both alone and synergistically in combination with certain monomeric quaternary ammonium salts.

The biofilm deactivation agents of the present invention are useful in a wide variety of aqueous systems, including but not necessarily limited to recreational and industrial systems, including aqueous base drilling systems. Industrial systems in which the present invention may be used include, but are not necessarily limited to cooling water systems used in power generating plants, refineries, chemical plants, air conditioning systems, process systems used to manufacture pulp, paper, paperboard, and textiles, particularly water laid nonwoven fabrics.

A wide variety of alkylamines are capable of deactivating biofilm bacteria according to the present invention if they are used at a high enough concentration. Suitable alkylamines are those with a "minimum biofilm eradication concentration" (MBEC) of about 200 or less, preferably about 100 ppm or less, more preferably about 50 ppm or less, and most preferably about 30 ppm or less.

The MBEC is a valuable measurement for determining whether the quantity of given agent that will be required to eradicate a biofilm will be economically and environmentally feasible. The MBEC test was developed by the University of Calgary to evaluate the efficacy of antibiotics and biocides towards biofilms. H. Ceri, et. al., "The MBEC Test: A New In Vitro Assay Allowing Rapid Screening for Antibiotic Sensitivity of Biofilm", *Proceedings of the ASM*, 98, p 525 (1998). Ceri, et. al., "Antifungal and Biocide Susceptibility testing of Candida Biofilms using the MBEC Device," Proceedings of the Interscience Conference on Antimicrobial Agents and Chemotherapy, vol. 38, p. 495 (1998); H. Ceri, et. al., "The Calgary Biofilm Device: A New Technology for the Rapid Determination of Antibiotic Susceptibility of Bacterial Biofilms," *Journal of Clinical Microbiology* 37 (1999) 1771–1776. The exclusive license for the MBEC technique is believed to be held by MBEC Biofilm Technologies, 665—8th Street S.W., Calgary, Alberta T2P 4H5 Canada.

The MBEC technique consists of growing identical 24-hour biofilms on 96 pegs arrayed in 12 rows and 8 columns. The biofilms then are challenged with decreasing concentrations of selected antibiotics and/or biocides. After a certain challenge time (generally one hour), the biofilms are placed in 96 individual wells of growth media and ultra-sonicated to deactivate any surviving organisms. After culturing overnight, the wells are checked for turbidity. Clear, transparent wells indicate complete deactivation of the biofilm. Conversely, turbidity ("growth") indicates lack of complete deactivation of the biofilm.

The minimum biofilm deactivation concentration (MBEC) is defined as the minimum concentration of an agent that completely deactivates biofilm bacteria. The MBEC technique provides a potentially powerful and reproducible tool to study the efficacy of biocides and additives towards biofilm deactivation. Unless otherwise indicated, the biofilms used in the examples below consisted of a pure culture of Pseudomonas aeruginosa (ATCC 15442). The reason for this is that Pseudomonas aeruginosa often represents the major biofilm component in industrial and recreational water systems. J. W. Costerton and H. Anwar, "Pseudomonas aeruginosa: The Microbe and Pathogen", in "Pseudomonas aeruginosa Infections and Treatment", A. L. Baltch and R. P. Smith (eds), Marcel Dekker, New York, 1994. In addition, Pseudomonas aeruginosa is a gram-negative bacteria. Gram-negative bacteria tend to be more difficult to kill than gram-positive bacteria. In other words, if an agent is effective against Pseudomonas aeruginosa, then persons of ordinary skill in the art would find it reasonable to predict that the agent also would be effective against other microorganisms found in biofilms.

As a general rule of thumb, about 1 pound of a biofilm treatment agent will result in 10 ppm of actives in a 12,000 gallon aqueous system. Alkylamines and blends that are suitable for use in the invention have MBEC's of about 200 ppm or less, and require about 20 pounds of the alkylamine or blend to effectively treat about 12,000 gallons of water. Preferred alkylamines or blends have the following characteristics: an MBEC of about 100 ppm or less, requiring about 10 pounds/12,000 gallons of water; more preferably an MBEC of about 50 ppm or less, requiring about 5 pounds/12,000 gallons of water; and, an MBEC of about 30 ppm or less requiring about 3 pounds/12,000 gallons of water.

The alkyl group of alkylamines that will produce an MBEC of 200 ppm or less have from about 8 to about 16 carbon atoms, more preferably from about 10 to about 16, even more preferably from about 11 to about 15 carbon atoms, and most preferably from about 12 to about 14 carbon atoms. Preferred alkylamines are primary alkylamines. Dimethylalkylamines also may satisfy the 200 ppm MBEC requirement when the alkyl group has from about 10 to about 16 carbon atoms, preferably from about 12 to about 16 carbon atoms.

MBEC and carbon number are two ways to identify alkylamines that are useful in the present invention. Another way to identify a suitable alkylamine is by its octanol/water coefficient. The octanol/water partition coefficient—$K_{ow}$—is defined as the ratio of the solute concentration in the octanol phase to that in the water phase. It is usually expressed as the logarithm of the number. A $logK_{ow}$ of 3.0 means that the compound is 1000 times more soluble in octanol than water. High $K_{ow}$ values can be an indicator of bioaccumulation whereby organisms retain a certain amount of a compound in their tissue. Octanol was chosen since it "mimics" the lipids found in organisms and thus forms the basis for a simple assay for potential biological interactions.

The following are calculated octanol/water partition coefficients for selected alkylamines and quaternary amines. Where available, experimentally determined values also are given [from N. Bodor, Z. Gabanyi, and C-K. Wang, Journal of the American Chemical Society, 111, 3783–3786 (1989)]. The calculated values were arrived at using the KowWIN program of the Environmental Science Center of Syracuse Research Corporation (http://esc.syrres.com/esc.htm).

| Compound | $logK_{ow}$ calculated | $logK_{ow}$ experimental |
|---|---|---|
| Alkylamines | | |
| 1-Butylamine | 0.97 | 0.87 |
| 1-Hexylamine | 1.82 | |
| 1-Octylamine | 2.80 | |
| 1-Decylamine | 3.78 | |
| 1-Dodecylamine | 4.76 | |
| 1-Tetradecylamine | 5.75 | |
| 1-Hexadecylamine | 6.73 | |
| Alkyldimethylamines (ADMAs) | | |
| N,N-Dimethylbutylamine | 1.51 | 1.70 |
| N,N-Dimethylhexylamine | 2.49 | |
| N,N-Dimethyloctylamine | 3.48 | |
| N,N-Dimethyldecylamine | 4.46 | |
| N,N-Dimethyldodecylamine | 5.44 | |
| N,N-Dimethyltetradecylamine | 6.42 | |
| N,N-Dimethylhexadecylamine | 7.41 | |
| Dialkylamines | | |
| N,N-Dibutylamine | 2.77 | 2.76 |
| N,N-Dipentylamine | 3.76 | |
| N,N-Dihexylamine | 4.74 | |
| N,N-Dioctylamine | 6.70 | |
| Alkyldimethylbenzylammonium Chlorides (ADBACS) | | |
| Octyldimethylbenzylammonium chloride | 0.96 | |
| Decyldimethylbenzylammonium chloride | 1.95 | |
| Dodecyldimethylbenzylammonium chloride | 2.93 | |
| Tetradecyldimethylbenzylammonium chloride | 3.91 | |
| Hexadecyldimethylbenzylammonium chloride | 4.89 | |
| Octadecyldimethylbenzylammonium chloride | 5.87 | |
| Eicosyldimethylbenzylammonium chloride | 6.86 | |
| Dialkyldimethylammonium Chlorides (DIDACs) | | |
| Dioctyldimethylammonium chloride | 2.69 | |
| Didecyldimethylammonium chloride | 4.66 | |
| Didodecyldimethylammonium chloride | 6.62 | |

Octanol water coefficients may be measured or calculated using a variety of known methods. The values herein were calculated using the LogKow program developed by the Syracuse Research Center, which may be found on the internet at http://esc.syrres.com/~esc/logkow.htm. The Log Kow program estimates the log octanol/water partition coefficient (log P) of organic chemicals using the atom/fragment contribution method. Based on the results of these calculations, persons of ordinary skill in the art would expect alkylamines having a calculated partition coefficient of from about 3.5 to about 7.5 to have an MBEC of about 200 ppm or less. Persons of ordinary skill in the art also would expect alkylamines having a calculated partition coefficient of from about 4 to about 6 to have an MBEC that is about 100 ppm or less, preferably 50 ppm or less, and more preferably 30 ppm or less.

Suitable alkylamines are commercially available from Aldrich Chemicals Ltd. or Sigma Chemical Company. Persons of ordinary skill in the art also can make alkylamines using known procedures, such as those described in R. Morrison and R. Boyd. Organic Chemistry (5th Ed. 1987) §§ 26.11–26.13, pp. 945–948, incorporated herein by reference. Dodecylamine also is available from Akzo, Nobel Chemicals Inc. The alkylamines of the present invention are useful alone, or preferably combination with a suitable quaternary ammonium salt. Suitable quaternary ammonium salts are available from a number of sources, including Albemarle Corporation. Suitable combinations of quaternary ammonium salts and alkylamines have an MBEC of about 200 ppm or less, more preferably about 100 ppm or less, even more preferably about 50 ppm or less, and most preferably about 30 ppm or less.

The ratio of alkylamine to the quaternary ammonium salt may be from about 10:1 to about 1:10. Preferably, the ratio is about 1:1. A preferred embodiment is a 1:1 ratio of a primary alkylamine having from about 10 to about 16 carbon atoms to a quaternary ammonium salts comprising substituent groups on the nitrogen atom independently selected from the group consisting of benzyl groups and alkyl groups having from about 8 to about 16 carbon atoms, preferably from about 10 to about 12 carbon atoms, provided that no more than one of said substituent groups comprises a benzyl group. Even more preferably, the primary alkylamine has from about 12 to about 14 carbon atoms and the quaternary ammonium salt is a dialkyldimethyl quaternary ammonium salt wherein the alkyl groups have from about 10 to about 12 carbon atoms. A most preferred embodiment is didecyldimethyl-ammonium chloride with a primary alkylamine having from about 12 to about 14 carbon atoms, most preferably tetradecylamine, most preferably at a 1:1 ratio. Preferably, the quaternary ammonium compound either has a calculated partition coefficient of from about 3.5 to about 7.5, more preferably from about 4 to about 6, or the combination of a selected alkylamine and a selected quaternary ammonium compound has such a calculated partition coefficient.

Although the alkylamine or the combination of alkylamine and quaternary ammonium salt may be used as the sole treatment in a water system to deactivate biofilms, the treatment of the present invention also is useful in systems containing oxidizing agents, including but not necessarily limited to HOBr and HOCl. In a preferred embodiment, the oxidizing agents are used in an amount effective to maintain static control of an aqueous system, and the non-oxidizing agents of the present invention are provided at intervals in order to deactivate any biofilms that may develop in the system.

The invention will be better understood with reference to the following examples, which are illustrative only and should not be construed as limiting the invention to a specific embodiment.

EXAMPLE 1

A series of tests was performed to assess the MBEC of a variety of biocides. The tests included, among others: chlorine- and bromine-based oxidizing biocides; several commercially available non-oxidizing biocides, such as glutaraldehyde and THPC (tetrakis(hydroxymethyl)-phosphonium chloride); and, the several alkylamines, namely octylamine, and dodecylamine.

The following protocol was used during the testing:

Section A—Preparation and Activity Testing of Biocide Formulations

Preparation of Synthetic Water

Synthetic water (SW) was prepared by adding 0.22 g $CaCl_2$, 0.168 g $NaHCO_3$, and 0.014 g NaCl to 1 L of deionized, distilled water (DDW). The mixture was sterilized by filtration through a 0.2 μm filter. The pH of this solution was 7.9 to 8.1 units and afforded a water containing 200 ppm Ca hardness (as $CaCO_3$), 150 ppm of alkalinity (as $CaCO_3$), and 150 ppm of chloride.

Preparation of 400 ppm Octylamine Solution

The stock 2500 ppm solution of octylamine in SW was prepared by diluting 0.05 g octylamine to 20.0 g in SW. A cloudy mixture resulted. To help solubilize the amine, 5 drops of 4% aq. HCl was added. This afforded a slightly cloudy solution with some foam which was stirred continuously prior to diluting 3.2 g of stock to 20.0 g with SW.

Preparation of 100 ppm Dodecylamine Solution

Stock 2500 ppm dodecylamine was prepared by diluting 0.038 g to 15.2 g in SW. About 5 drops of 4% aq. HCl was added and the mixture was heated and stirred to aid dissolution (dodecylamine is a solid at room temperature). This yielded a pearlescent suspension which was continually stirred prior to diluting 0.80 g of the stock solution to 20.0 g with SW.

Stock 400 ppm Glutaraldehyde Solution

Glutaraldehyde (0.159 g, Aldrich 50 wt.%) was diluted to 19.9 g with SW. The solution (1.99 g) was further diluted to 19.9 g with SW, providing a nominal 400 ppm glutaraldehyde solution for biofilm challenge.

Preparation of 200 ppm Tetrakis(hydroxymethyl) phosphonium Chloride Solution (THPC) THPC (0.125 g, Aldrich 80% active) was diluted to 10.0 g with SW. A portion of this solution (0.40 g) was diluted to 20.0 g with SW to provide a 200 ppm THPC solution for biofilm challenge.

General Procedure—Preparation of Quaternary Ammonium Chloride Solutions

The quats used in this work were all 50% active and consisted of Albemarle BQ 451-5 biocide, BQ 361-5 biocide, AC 76-5 biocide, and DAQ 1010-5 biocide. The following table provides the chemical composition of these quats. Quat solutions of 800 ppm activity were prepared from BQ 451, BQ 361, and AC 76 biocides by diluting the equivalent of 40 mg quat to 25 mL with SW. A solution of DAQ 1010 with 400 ppm activity was prepared by diluting the equivalent of 20 mg quat to 25 mL with SW.

| | Chemical Compositions of Quaternary Amines |
|---|---|
| Quat | Chemical Composition |
| BQ 451-5 | n-Alkyldimethylbenzyl ammonium chloride (n-alkyl = 40% $C_{12}$, 50% $C_{14}$, 10% $C_{16}$) |
| BQ 361-5 | n-Alkyldimethylbenzyl ammonium chloride (n-alkyl = 67% $C_{12}$, 25% $C_{14}$, 7% $C_{16}$, 1% $C_{18}$) |
| AC 76-5 | 49.8% n-Alkyldimethylbenzyl ammonium chloride (n-alkyl = 60% $C_{12}$, 30% $C_{16}$, 5% $C_{12}$, 5% $C_{18}$); 0.2% n-Dialkylmethylbenzyl ammonium chloride (n-alkyl as above) |
| DAQ 1010-5 | Didecyldimethyl ammonium chloride |

Section B—Microbiological Procedures

Biofilm Preparation and Biocide Challenge

*Pseudomonas aeruginosa* (ATCC 15442) biofilms were prepared on the 96 pegs of the MBEC plate by aerobic incubation in simple salts medium with 0.1% glucose (24 hours, 35° C.). The pegs were rinsed in synthetic water (SW) and then challenged by the biocide for one hour. Following the biocide challenge, the pegs were rinsed twice with SW and then sonicated into Mueller-Hinton broth (225 μL per well). The broth was then incubated for 18 hours at 35° C.

Determination of Minimum Biofilm Deactivation Concentration

After the 18 hour incubation period, the recovery wells were checked for turbidity. Clear, transparent wells indicated complete deactivation of the biofilm. Conversely, turbidity indicated the lack of complete deactivation of the biofilm. The minimum biofilm deactivation concentration (MBEC) is defined as the minimum concentration of agent which results in complete deactivation of the biofilm. MBEC endpoints were unambiguously determined by absorbance at 650 nm. using UV visible spectroscopy. An absorbance >0.100 was considered a positive indication of growth.

MBEC values for duplicate runs on the same plate were typically the same. In cases where duplicate runs were not the same, the difference almost always represented just one 50% dilution in biocide concentration or one well of the 96 well plate.

Control Data

Formulations in all of this work were run in duplicate together with suitable controls. Various microbiological controls and checks also were run to assure the integrity of the experimental methods employed. For example, initial and final concentrations of inocula used to grow the biofilms (McFarland =1.0) were checked using serial plating.

In addition to the above work, 12 peg sites (representing row 8 on each MBEC plate) also were used for various control purposes. The biocide plates contained just synthetic water (no biocide) in row 8. Sterility controls were run by removing MBEC pegs in row 8, columns 1–3 prior to growth of the biofilm. These were then taken through the entire procedure. Since no biofilm could grow (pegs removed), no turbidity (indicates viable bacteria) should be observed. 24-Hour biofilm controls were determined by removing pegs 4–6, row 8 immediately after 24 hour biofilm growth. The pegs were sonicated in saline to remove the biofilm and serially plated. Biocide challenge controls were determined by removing pegs 7–9, row 8 following biocide challenge and treating the pegs as 4–6 above. Turbidity controls were run by taking pegs 10–12 through the entire MBEC procedure. Since the biofilms saw no biocide (only synthetic water), these samples should turn turbid.

The control data indicated no unusual circumstances or contamination during these experiments. The average biofilm concentration on the pegs was $1.0 \times 10^7$ CFUs/peg.

Determination of Minimum Biofilm Eradication Concentration

The activities of octylamine and dodecylamine were tested individually. We also tested glutaraldehyde and tetrakis(hydroxymethyl)phosphonium chloride (THPC) for comparison purposes. Results are summarized in the following Table (see table in attachment).

| Biocide Formulation | MBEC, ppm | MBEC, avg. |
|---|---|---|
| n-octylamine | 400, 400 | 400 |
| n-dodecylamine | 25, 25 | 25 |
| glutaraldehyde | 50, 50 | 50 |
| THPC | 100, 100 | 100 |
| BQ 451 | 50, 50 | 50 |
| BQ 361 | 100, 50 | 75 (a) |
| AC 76 | 100, 50 | 75 |
| DAQ 1010 | 100, 25 | 50 |

(a) Growth at 200 ppm $Cl_2$ level in one case.

Surprisingly, dodecylamine proved extremely effective at biofilm deactivation (MBEC=25 ppm). The length of the alkyl group of the alkylamine apparently plays a critical role as octylamine (MBEC=400 ppm) was much less active than dodecylamine (MBEC=25 ppm). Dodecylamine was more active than any other single non-oxidizing biocide tested in this work.

EXAMPLE 2

A series of primary fatty amines with alkyl groups having a variety of carbon atom lengths and configurations were tested. The following protocols were used in these tests. Note: Unless otherwise specified, all chemicals were purchased from Sigma-Aldrich, Canada and used without further purification.

Section A—Preparation and Activity Testing of Biocide Formulations

Preparation of Synthetic Water

Synthetic water (SW) was prepared as in Example 1.

Preparation of Primary Alkylamine Solutions

Stock 2500 ppm solutions were prepared by diluting 0.05 g alkylamine to 20 g with SW. It was necessary to add at least one drop of acid (38% aq. HCl) to obtain stable solutions from amines of $C_{10}$ alkyl chain length and higher. Solutions for MBEC tests were prepared by further diluting the appropriate amount of stock solution with SW.

Preparation of Alkyldimethylamine (ADMA) Solutions

Stock 2500 ppm solutions of alkyldimethylamines were prepared as above by diluting ADMA (0.05 g) to 20 g with SW. It was necessary to add one drop of acid (38% aq. HCl) to all of the systems to obtain stable solutions. Further dilution of the stock solutions with SW afforded the solutions needed for MBEC tests. All the ADMA® amines used in this work were supplied by Albemarle Corporation.

Preparation of Dialkylmethylamine (DAMA) Solutions

Stock 2500 ppm solutions of dialkylmethylamines were formulated as described above for the alkyldimethylamines. The didecylmethylamine (DAMA® 1010 amine) was supplied by Albemarle Corporation.

Preparation of Secondary Alkylamine Solutions

Solutions of containing 1600 ppm dibutyl-, dipentyl-, and dihexylamines were prepared by diluting 0.032 g of amine to 20 g with SW. It was necessary to add 1 drop acid (38% aq. HCl) in order to obtain stable solutions with dipentyl- and dihexylamine.

Section B—Microbiological Procedures

Biofilm Preparation and Biocide Challenge

*Pseudomonas aeruginosa* (ATCC 15442) biofilms were prepared as described in Example I. The 7-day biofilms were prepared by a modification of the above procedure. Each day, spent media was replaced with fresh media and inocula.

Determination of Minimum Biofilm Eradication Concentration

The MBEC was determined using the same procedure as in Example 1. The following Table gives the dosing for the biocides and controls to investigate the series of primary fatty amines.

| $C_6H_{13}NH_2$ | $C_8H_{17}NH_2$ | $C_{10}H_{21}NH_2$ | $C_{12}H_{25}NH_2$ | $C_{14}H_{29}NH_2$ | $C_{16}H_{33}NH_2$ |
|---|---|---|---|---|---|
| Control | Control | Control | Control | Control | Control |
| 25 ppm | 12 ppm | 6 ppm | 3 ppm | 3 ppm | 3 ppm |
| 50 ppm | 25 ppm | 12 ppm | 6 ppm | 6 ppm | 6 ppm |
| 100 ppm | 50 ppm | 25 ppm | 12 ppm | 12 ppm | 12 ppm |
| 200 ppm | 100 ppm | 50 ppm | 25 ppm | 25 ppm | 25 ppm |
| 400 ppm | 200 ppm | 100 ppm | 50 ppm | 50 ppm | 50 ppm |
| 800 ppm | 400 ppm | 200 ppm | 100 ppm | 100 ppm | 100 ppm |
| 1600 ppm | 800 ppm | 400 ppm | 200 ppm | 200 ppm | 200 ppm |

Control Data

Formulations in all of this work were run in duplicate together with suitable controls. Various microbiological controls and checks again were run to assure the integrity of the experimental methods employed. For example the final concentrations of inocula broth used to grow the biofilms were checked using serial plating techniques. In addition, 12 peg sites (representing row 8 on each MBEC plate) also were used for various control purposes. The data indicated no unusual circumstances or contamination occurred during these experiments. The average biofilm population for the plates used in this study range from 1.0 to $1.8 \times 10^7$ CFU's/peg.

A. $C_6$, to $C_{16}$, Primary Fatty Amines

The following Table presents MBEC results for one-hour exposures of the series of $C_6$ to $C_{16}$, primary fatty amines. Activity increased with alkyl chain length UP to $C_{14}$ and then decreased at $C_{16}$. Dodecylamine and tetradecylamine were by far the most effective compounds in the series with MBECs of 38 and 25 ppm, respectively. Decylamine and hexadecylamine were next in activity with MBECs of 200 ppm for both.

| | 1 Hour Contact | |
|---|---|---|
| Biocide System | MBEC, ppm | MBEC, avg. |
| $C_6H_{13}NH_2$ | 1600, 1600 | 1600 |
| $C_8H_{17}NH_2$ | 400, 400 | 400 |
| $C_{10}H_{21}NH_2$ | 200, 200 | 200 |
| $C_{12}H_{25}NH_2$ | 25, 50 | 38 |
| $C_{14}H_{29}NH_2$ | 25, 25 | 25 |
| $C_{16}H_{33}NH_2$ | 200, 200 | 200 |

B. Alkyldimethylamines

A series of alkyldimethylamines, commercially available from Albemarle Corporation as ADMA® amines, having from about 8 to about 18 carbon atoms were tested for activity against biofilm bacteria. These alkyldimethylamines did not eradicate biofilm at the maximum test concentrations of 200 to 800 ppm. The following Table highlights MBEC results, which indicate that these compounds exhibit a much lower activity relative to the primary fatty amines having 12 and 14 carbon atoms discussed above. ADMA 14 and ADMA 16 amines showed evidence of biofilm deactivation at 200 ppm (as indicated by regrowth optical density measurements). We estimate the MBECs for these compounds as 400 to 800 ppm--which means that these alkyldimethylamines were an order of magnitude less active than the best performing primary fatty amines.

| | 1 Hour Contact | |
|---|---|---|
| Biocide System | MBEC, ppm | MBEC, avg. |
| ADMA 8 Amine | >800, >800 | >800 |
| ADMA 10 Amine | >400, >400 | >400 |
| ADMA 12, 14, 16, or 18 Amine | >200, >200 | >200 |

C. Dialkylmethylamines

A series of dialkylmethylamines with alkyl groups having from about 4 to about 10 carbon atoms were tested for activity. None of the dialkylmethylamines tested eradicated the biofilm at 200 ppm or less. The following Table compares the activities of several dialkyl and dialkylmethylamines.

| | 1 Hour Contact | |
|---|---|---|
| Biocide System | MBEC, ppm | MBEC, avg. |
| $CH_3(C_4H_9)_2N$ | >800, >800 | >800 |
| $CH_3(C_6H_{13})_2N$ | >800, >800 | >800 |
| $CH_3(C_8H_{17})_2N$ | 800, 800 | 800 |
| DAMA 1010 Amine $(CH_3(C_{10}H_{21})_2N)$ | 400, 400 | 400 |
| $(C_4H_9)_2NH$ | >1600, >1600 | >1600 |
| $(C_6H_{13})_2NH$ | >1600, 1600 | ~2400 |
| $(C_8H_{17})_2NH$ | 1600, 1600 | 1600 |

Albemarle's DAMA® 1010 amine (didecylmethylamine) performed the best (MBEC=400 ppm). The octyl analog was second in terms of activity (MBEC=800 ppm). As with the primary fatty amines, alkyl chain length played an important role in activity. Dioctylmethylamine had an MBEC of 800 ppm; the dihexyl and dibutyl analogs had MBECs of>800 ppm.

Secondary dialkylamines generally displayed low activity. The MBEC of dioctylamine, for example, was 1600 ppm. The MBEC of dihexylamine was estimated at 2400 ppm.

EXAMPLE 3

Older biofilms offer increased resistance to biocides. Studies were extended to 7-day biofilms formed using *P. aeruginosa*. The procedure used to form the 7-day biofilm was the same as in Example 1, except that each day, spent media was replaced with fresh media and inocula. This biofilm was then challenged with oxidizing and non-oxidizing biocides.

The stock hypochlorous acid solution was prepared from sodium hypochlorite solution (0.41, >4%, actual ~2.7%) diluted to 100 g with SW. The solution was stored in a 4 oz. amber glass bottle in the refrigerator. Stock hypobromous acid was blended from sodium hypochlorite (0.42 g, 0.15 mmol ) as above and sodium bromide (0.028 g, 0.27 mmol). The solution was also stored in a 4 oz. amber glass bottle in the refrigerator overnight. The halogen donor solutions were prepared by dissolving BCDMH (0.0054 g), DBDMH (0.0054 g), or trichloroisocyanuric acid (0.0033 g) in 20 g SW with stirring.

The stock solution was diluted about 1:10 for MBEC testing. The solutions were further characterized by performing another 1:10 dilution and analyzing for free or total chlorine by the DPD method using a Hach DR 700 spectrophotometer. The actual starting oxidant levels are shown in the following Table:

| Actual Levels of Oxidizing Biocides used with 7-Day Biofilms | | | | |
|---|---|---|---|---|
| Biocide | Stock Solution, g | SW, g | Free $Cl_2$, ppm | Total $Cl_2$, ppm |
| HOCl | 1.99 | 19.9 | 10.4 | |
| HOBr | 1.98 | 19.8 | | 10.1 |
| BCDMH | 2.39 | 20.0 | | 9.1 |
| Trichlor | 1.01 | 10.1 | 10.6 | |

The 7-day biofilm proved more difficult to eradicate than 24-hour biofilms. Initial results indicated that several formulations failed to deactivate the biofilm at the initial concentrations employed. We therefore challenged a second plate with higher concentrations of biocides (Example 4).

EXAMPLE 4

Another 7-day biofilm was prepared from *P. aeruginosa*, as in EXAMPLE 3. This biofilm was then challenged with several common oxidizing and non-oxidizing biocides.

The results are given in the following Table:

Performance of Selected Biocides Towards a 7-Day Biofilm

| Biocide System | 1 Hour Contact- Example 3 MBEC, ppm | 1 Hour Contact- Example 3 MBEC, avg. | 1 Hour Contact- Example 4 MBEC, ppm | 1 Hour Contact- Example 4 MBEC, avg. |
|---|---|---|---|---|
| $Cl_2$ (from NaOCl) | >10, >10 | >10 | 20, 20 | 20 |
| $Br_2$ (from NaOCl + NaBr) | 5, 10 | 7.5 | | |
| $Br_2$ (from BCDMH) | 5, 10 | 7.5 | | |
| $Cl_2$ (from Trichlor) | 5, >10 | | 20, 20 | 20 |
| Glutaraldehyde | 100, >200 | ~200 | | |
| $C_{12}H_{25}NH_2$ | | | 100, 50 | 75 |
| DAQ 1010 | | | 100, 50 | 75 |

Notes:
Values in ppm oxidant (as $Cl_2$) or as ppm active

Br-based biocides in general were more active than Cl-based biocides. For example, the Cl-based biocides bleach or trichlor required 20 ppm residual to completely deactivate the biofilm. The data indicate that the Br-based biocides are more effective than Cl-based biocides against aged, more-difficult-to kill biofilms.

The MBEC for glutaraldehyde on a 7-day biofilm was about 200 ppm, compared to 50 to 100 ppm on 24-hour biofilms. Dodecylamine and DAQ 1010 required about twice the concentration to kill the 7-day biofilm (MBECs=75 ppm) as for the 24-hour biofilm (MBECs ~38 ppm from previous work).

EXAMPLE 5

Certain fatty amines were tested in combination with the Albemarle quat DAQ 1010 (didecyldimethyl-ammonium chloride). Test solutions were prepared using initial concentrations of 100 ppm of each material and then successively diluted with synthetic water in the MBEC device.

The data in the following Table indicates that the combination of DAQ 1010 and $C_{14}$ fatty amine gave the best performance of any non-oxidizing biocide system tested so far. Just 12.5 ppm total biocide completely eradicated biofilm bacteria. This compares with values of about 38 ppm for DAQ 1010 alone and 25 ppm for $C_{14}$ fatty amine alone (FIG. 6).

Activities of Quat/Amine Blends
[MBECs for blends based on total amount of components (1:1 ratio)]

| Biocide System | 1 Hour Contact MBEC, ppm | 1 Hour Contact MBEC, avg. |
|---|---|---|
| DAQ 1010 (1) | 25, 50 | 38 |
| DAQ 1010 + $C_{10}H_{21}NH_2$ | 200, 25 | ~76 |
| DAQ 1010 + $C_{12}H_{25}NH_2$ | 25, 25 | 25 |
| DAQ 1010 + $C_{14}H_{29}NH_2$ (2) | 12, 12 | 12 |
| $C_{14}H_{29}NH_2$ | 25, 25 | 25 |

(1) Previous work
(2) Growth at 25 ppm in one case

The combinations of quaternary ammonium compounds, specifically Albemarle quat DAQ 1010 (didecyldimethylammonium chloride) and primary fatty amines proved very effective against biofilm bacteria. The DAQ 1010 and tetradecylamine mixture was highly active against biofilm bacteria and one of the best performing non-oxidizing biocide systems (MBEC=12.5 ppm total additive loading—6.2 ppm each).

Persons of ordinary skill in the art will recognize that many modifications may be made to the present invention without departing from the spirit and scope of the invention. The embodiment described herein is meant to be illustrative only and should not be taken as limiting the invention, which is defined in the following claims.

What is claimed is:

1. An aqueous system in contact with at least one surface susceptible to buildup thereon of biofilm, wherein said aqueous system is treated with a quantity of a biofilm deactivation agent consisting essentially of one or more alkylamines having a minimum biofilm deactivation concentration, if and when tested with a pure culture of *Pseudomonas aeruginosa*, of about 200 ppm or less, said quantity being effective to control buildup of said biofihn on said surface, and wherein said aqueous system contains a quantity of an oxidizing agent effective to maintain static control over said system.

2. The aqueous system of claim 1 wherein said system is an aqueous industrial system, an aqueous recreational system, or an aqueous drilling system.

3. The aqueous system of claim 2 wherein said one or more alkylamines are one or more primary alkylamines in which the alkyl group has from about 10 to about 18 carbon atoms.

4. The aqueous system of claim 3 wherein the alkyl group of said one or more primary alkylamines has from about 12 to about 14 carbon atoms.

5. The aqueous system of claim 3 wherein said minimum biofilm deactivation concentration is about 100 ppm or less.

6. The aqueous system of claim 2 wherein said minimum biofilm deactivation concentration is about 100 ppm or less.

7. The aqueous system of claim 2 wherein said minimum biofilm deactivation concentration is about 50 ppm or less.

8. The aqueous system of claim 2 wherein said minimum biofilm deactivation concentration is about 30 ppm or less.

9. An aqueous system in contact with at least one surface susceptible to buildup thereon of biofilm, wherein said aqueous system is treated with (i) one or more alkylamines and also (ii) one or more quaternary ammonium salts, (i) and (ii) each having a minimum biofilm deactivation concentration, if and when tested with a pure culture of *Pseudomonas aeruginosa*, of about 200 ppm or less, the quantity of(i) and (ii) used being effective to control buildup of said biofilm on said surface.

10. The aqueous system of claim 9 wherein said quaternary ammonium salt comprises substituent groups selected from the group consisting of no more than one benzyl group and alkyl groups independently selected from those having from about 8 to about 16 carbon atoms.

11. The aqueous system of claim 9 wherein said one or more quaternary ammonium salts are selected from the group consisting of (a) alkyldimethylbenzylammonium salts in which the alkyl is selected from those having from about 8 to about 16 carbon atoms, and (b) dialkyldimethylammonium salts in which each alkyl is independently selected from those having from about 8 to about 16 carbon atoms.

12. The aqueous system of claim 9 wherein said one or more quaternary ammonium salts is didecyldimethylammonium chloride.

13. The aqueous system of any of claims 9, 10, 11, or 12 wherein said one or more alkylamines is one or more primary alkylamines having from about 10 to about 18 carbon atoms.

14. The aqueous system of claim 13 wherein said one or more primary alkylamines is dodecylamine or tetradecylamine, or both.

15. The aqueous system of any of claims 9, 10, 11, or 12 wherein said aqueous system contains a quantity of an oxidizing agent effective to maintain static control over said aqueous system.

16. An aqueous system containing a biofilm-controlling quantity of an alkylamine biofilm deactivation agent having a minimum biofilm deactivation concentration, if and when tested with a pure culture of Pseudomonas aeruginosa, of about 200 ppm or less, and a quantity of an oxidizing agent effective to maintain static control over said aqueous system.

17. The aqueous system of claim 16 wherein said deactivation agent is one or more primary alkylamines having from about 10 to about 16 carbon atoms.

18. The aqueous system of claim 16 wherein said deactivation agent is one or more primary alkylamines having from about 12 to about 14 carbon atoms.

19. The aqueous system of any of claims 16, 17, or 18 wherein one or more quaternary ammonium salts have been added to said aqueous system.

20. An aqueous system selected from the group consisting of an industrial system, a recreational system, and a drilling system, said aqueous system comprising a quantity of a biofilm deactivation agent comprising a combination of one or more primary alkylamines and one or more quaternary ammonium salts, said agent, if and when tested with a pure culture of *Pseudomonas aeruginosa*, having a minimum biofilm deactivation concentration of about 100 ppm or less, said quantity being effective to achieve said minimum biofilm deactivation concentration in said system.

21. The aqueous system of claim 20 wherein said biofilm deactivation concentration is about 50 ppm or less.

22. The aqueous system of claim 20 wherein said biofilm deactivation concentration is about 20 ppm or less.

23. The aqueous system of claim 22 wherein the alkyl group of said one or more primary alkylamines has from about 12 to about 14 carbon atoms; and wherein said one or more quaternary ammonium salts are one or more dialkyldimethyl quaternary ammonium salts in which each of the alkyl groups other than methyl have from about 10 to about 12 carbon atoms.

24. An aqueous system in contact with at least one surface susceptible to buildup thereon of biofilm, wherein said aqueous system is treated with a quantity of a biofilm deactivation agent consisting essentially of one or more alkylamines having an octanol/partition coefficient of from about 3.5 to about 7.5, said quantity being effective to control buildup of said biofilm on said surface, and wherein said aqueous system contains a quantity of an oxidizing agent effective to maintain static control over said aqueous system.

25. The aqueous system of claim 24 wherein said octanol/partition coefficient is from about 4 to about 6.

26. An aqueous system into which biofilm deactivation agents have been added, wherein the deactivation agents used consist essentially of (i) one or more alkylamines having an octanol/partition coefficient of from about 3.5 to about 7.5, and (ii) one or more quaternary ammonium salts having an octanol/partition coefficient of from about 3.5 to about 7.5, the quantity of said deactivation agents used being effective to control buildup of biofilm on a surface in contact with said aqueous system.

27. The aqueous system of claim 26 wherein the octanol/partition coefficient of said one or more alkylamines is from about 4 to about 6, and wherein the octanol/partition coefficient of said one or more quaternary ammonium salts is from about 4 to about 6.

28. A method for treating an aqueous system in contact with one or more surfaces susceptible to buildup thereon of biofilm, said method comprising adding to said aqueous system a quantity of a biofilm eradicator comprising one or more alkylamines having a minimum biofilm deactivation concentration of about 200 ppm or less, in an amount to effectively challenge said biofilm, and providing to said aqueous system a quantity of an oxidizing agent effective to maintain static control over said aqueous system.

29. The method of claim 22 wherein at least one quaternary ammonium salt is also added to said aqueous system.

30. An aqueous system resistant to biofilm buildup on at least one surface in contact therewith, said resistance resulting from addition to the aqueous system of (i) at least one alkylamine selected from the group consisting of primary alkylamines in which the alkyl group has from about 10 to about 16 carbon atoms and dimethylalkylamines in which the alkyl group other than the methyl groups has from about 12 to about 18 carbon atoms, and (ii) at least one quaternary ammonium salt selected from the group consisting of alkyldimethylbenzyl ammonium salts and dialkyldimethylammonium salts, (i) and (ii) being added in quantities effective to control buildup of said biofilm on said surface.

31. The aqueous system of claim 30 wherein the at least one quaternary ammonium salt added to said system is didecyldimethylamine.

32. The aqueous system of claim 30 wherein the at least one alkylamine added to said system is at least one primary alkylamine having from about 10 to about 16 carbon atoms in the alkyl group.

33. The aqueous system of claim 30 wherein the at least one alkylamine added to said system is at least one primary alkylamine having from about 12 to about 14 carbon atoms in the alkyl group.

34. The aqueous system of claim 33 wherein the at least one quaternary ammonium salt added to said system is didecyldimethylamine.

35. The aqueous system of any of claims 30, 31, 32, 33, or 34 wherein said aqueous system contains a quantity of an oxidizing agent effective to maintain static control over said aqueous system.

* * * * *